(12) United States Patent
Kinlen

(10) Patent No.: US 12,290,617 B2
(45) Date of Patent: May 6, 2025

(54) PEROXIDE-GENERATING AIR PURIFICATION ELEMENT

(71) Applicant: The Boeing Company, Chicago, IL (US)

(72) Inventor: Patrick John Kinlen, Fenton, MO (US)

(73) Assignee: The Boeing Company, Arlington, VA (US)

( * ) Notice: Subject to any disclaimer, the term of this patent is extended or adjusted under 35 U.S.C. 154(b) by 818 days.

(21) Appl. No.: 17/303,773

(22) Filed: Jun. 7, 2021

(65) Prior Publication Data

US 2022/0054694 A1 Feb. 24, 2022

Related U.S. Application Data

(60) Provisional application No. 63/068,258, filed on Aug. 20, 2020.

(51) Int. Cl.
| | |
|---|---|
| *A61L 9/04* | (2006.01) |
| *A61L 9/12* | (2006.01) |
| *A61L 101/02* | (2006.01) |
| *B01D 53/78* | (2006.01) |
| *B64D 13/06* | (2006.01) |

(Continued)

(52) U.S. Cl.
CPC ............ *A61L 9/046* (2013.01); *A61L 9/12* (2013.01); *B01D 53/78* (2013.01); *B64D 13/06* (2013.01); *C25B 1/30* (2013.01); *C25B 9/23* (2021.01); *A61L 2101/02* (2020.08);

(Continued)

(58) Field of Classification Search
None
See application file for complete search history.

(56) References Cited

U.S. PATENT DOCUMENTS

| 7,842,637 B2 | 11/2010 | Ebron et al. |
| 7,959,773 B2 | 6/2011 | Hou et al. |

(Continued)

FOREIGN PATENT DOCUMENTS

WO 2008018856 A2 2/2008

OTHER PUBLICATIONS

Hou, S. et al., "Self-detoxifying polymer system for chemical and biological warfare agents," Abstract in the Proceedings of "234th American Chemical Society National Meeting," Aug. 19, 2007, Boston, MA, 1 pages.

(Continued)

*Primary Examiner* — Holly Kipouros
(74) *Attorney, Agent, or Firm* — Alleman Hall & Tuttle LLP

(57) ABSTRACT

A system includes an airflow passage and an air purification element. The airflow passage is configured to confine a flow of air and direct the flow of air toward a space. The air purification element is positioned in the airflow passage and configured to produce a peroxide to oxidize contaminants in air flowing through the airflow passage. The air purification element includes a peroxide-generating structure and a matrix containing a peroxide-activating catalyst configured to activate peroxide produced. The air purification element is configured to produce the peroxide from a water vapor and oxygen in the air within the airflow passage when energized by an energy source, and the matrix is configured to allow the contaminants to contact peroxide activated by the peroxide-activating catalyst.

20 Claims, 10 Drawing Sheets

(51) Int. Cl.
*C25B 1/30* (2006.01)
*C25B 9/23* (2021.01)

(52) U.S. Cl.
CPC ...... *A61L 2209/16* (2013.01); *A61L 2209/211* (2013.01); *B64D 2013/064* (2013.01); *B64D 2013/067* (2013.01)

(56) References Cited

U.S. PATENT DOCUMENTS

| | | | |
|---|---|---|---|
| 7,993,495 B2 | 8/2011 | Kinlen et al. | |
| 2002/0098109 A1* | 7/2002 | Nelson | A61L 2/10 422/123 |
| 2006/0104858 A1* | 5/2006 | Potember | A61L 9/205 422/123 |
| 2007/0114121 A1* | 5/2007 | Kinlen | A61L 2/03 423/584 |
| 2008/0170971 A1 | 7/2008 | Bergeron et al. | |
| 2009/0288945 A1 | 11/2009 | Hou et al. | |
| 2009/0288946 A1 | 11/2009 | Kinlen et al. | |
| 2009/0291843 A1 | 11/2009 | Ebron et al. | |
| 2009/0291844 A1 | 11/2009 | Hou et al. | |
| 2010/0010285 A1 | 1/2010 | Ebron et al. | |
| 2010/0095697 A1* | 4/2010 | Morioka | C09D 5/1625 524/401 |
| 2010/0226943 A1* | 9/2010 | Brennan | B08B 17/06 428/141 |
| 2017/0197493 A1* | 7/2017 | Paranhos | A61L 2/10 |
| 2018/0250431 A1* | 9/2018 | Eide | A61L 9/046 |

OTHER PUBLICATIONS

"Vertical cyclone," Wikimedia.org, Available Online at https://upload.wikimedia.org/wikipedia/en/6/6d/Vertical-cyclone.jpg, Available as Early as Feb. 15, 2019, 1 page.
European Patent Office, Extended European Search Report Issued in Application No. 21191518.6, Jan. 25, 2022, Germany, 7 pages.

* cited by examiner

PEROXIDE-GENERATING AIR PURIFICATION ELEMENT

CROSS REFERENCE TO RELATED APPLICATIONS

This application claims priority to U.S. Provisional Patent Application Ser. No. 63/068,258, filed Aug. 20, 2020, the entirety of which is hereby incorporated herein by reference for all purposes.

FIELD

The present disclosure relates generally to air purification, and more specifically, to peroxide-generating air purification elements for treating airflow into enclosed spaces.

BACKGROUND

Air contaminated with pathogens and/or toxins poses a significant risk to human health, as people may become ill upon inhalation of such contaminants. Thus, disinfection of air such air may help to reduce the impact of such contaminants on human health. However, conventional disinfectant methods have limitations. For example, conventional disinfectants can include undesirable substances. Further, filters can become clogged over time, and may be only partially effective at removing contaminants from air.

Activated peroxide can destroy microorganisms such as bacteria, viruses, and fungi, toxins produced by microorganisms, and myriad chemical agents, yet remains safe for human use.

SUMMARY

To address the above issues, according to one aspect of the present disclosure, a system is provided herein. In this aspect, the system includes an airflow passage and an air purification element. The airflow passage is configured to confine a flow of air and direct the flow of air toward a space. The air purification element is positioned in the airflow passage and configured to produce a peroxide to oxidize contaminants in air flowing through the airflow passage. The air purification element includes a peroxide-generating structure and a matrix containing a peroxide-activating catalyst configured to activate peroxide produced. The air purification element is configured to produce the peroxide from a water vapor and oxygen in the air within the airflow passage when energized by an energy source, and the matrix is configured to allow the contaminants to contact peroxide activated by the peroxide-activating catalyst.

Another aspect of the present disclosure relates to an aircraft. In this aspect, the aircraft includes a cabin, an airflow passage, and an air purification element. The airflow passage is configured to confine a flow of air and direct the flow of air toward the cabin. The air purification element is positioned in the airflow passage and configured to produce a peroxide to oxidize contaminants in air flowing through the airflow passage. The air purification element includes a peroxide-generating structure and a matrix. The peroxide-generating structure is configured to produce the peroxide from water vapor and oxygen in the airflow passage. The peroxide-generating structure includes a first electrode separated from a second electrode by an ionically conductive matrix and is configured to produce the peroxide upon application of a voltage across the first electrode and the second electrode. The matrix includes a peroxide-activating catalyst that activates the peroxide produced and is positioned to allow the contaminants to contact peroxide activated by the peroxide-activating catalyst.

Another aspect of the present disclosure relates to a method of oxidizing contaminants in air flowing through an airflow passage via an air purification element. In this aspect, the method includes directing a flow of air through the air purification element. The method includes energizing a peroxide-generating structure of the air purification element to produce a peroxide from water vapor and oxygen in the airflow passage. The method further includes activating, via a peroxide-activating catalyst, at least some of the peroxide produced, and contacting the air flowing through the airflow passage with the activated peroxide to oxidize the contaminants.

Still another aspect of the present disclosure relates to a replaceable air purification element. The replaceable air purification element includes a housing, a peroxide-generating structure, and a matrix. The housing is configured to be removably inserted into an airflow passage that confines a flow of air and directs the flow of air toward a space. The peroxide-generating structure is positioned within the housing and is configured to produce a peroxide from water vapor and oxygen in the air within the airflow passage when energized by an energy source. The matrix includes a peroxide-activating catalyst that activates the peroxide produced and is configured to allow contaminants in the flow of air to contact peroxide activated by the peroxide-activating catalyst.

The features, functions, and advantages discussed can be provided independently in various embodiments or may be combined in yet other embodiments, further aspects of which are described in detail with reference to the following description and drawings.

DETAILED DESCRIPTION

Figure 1:
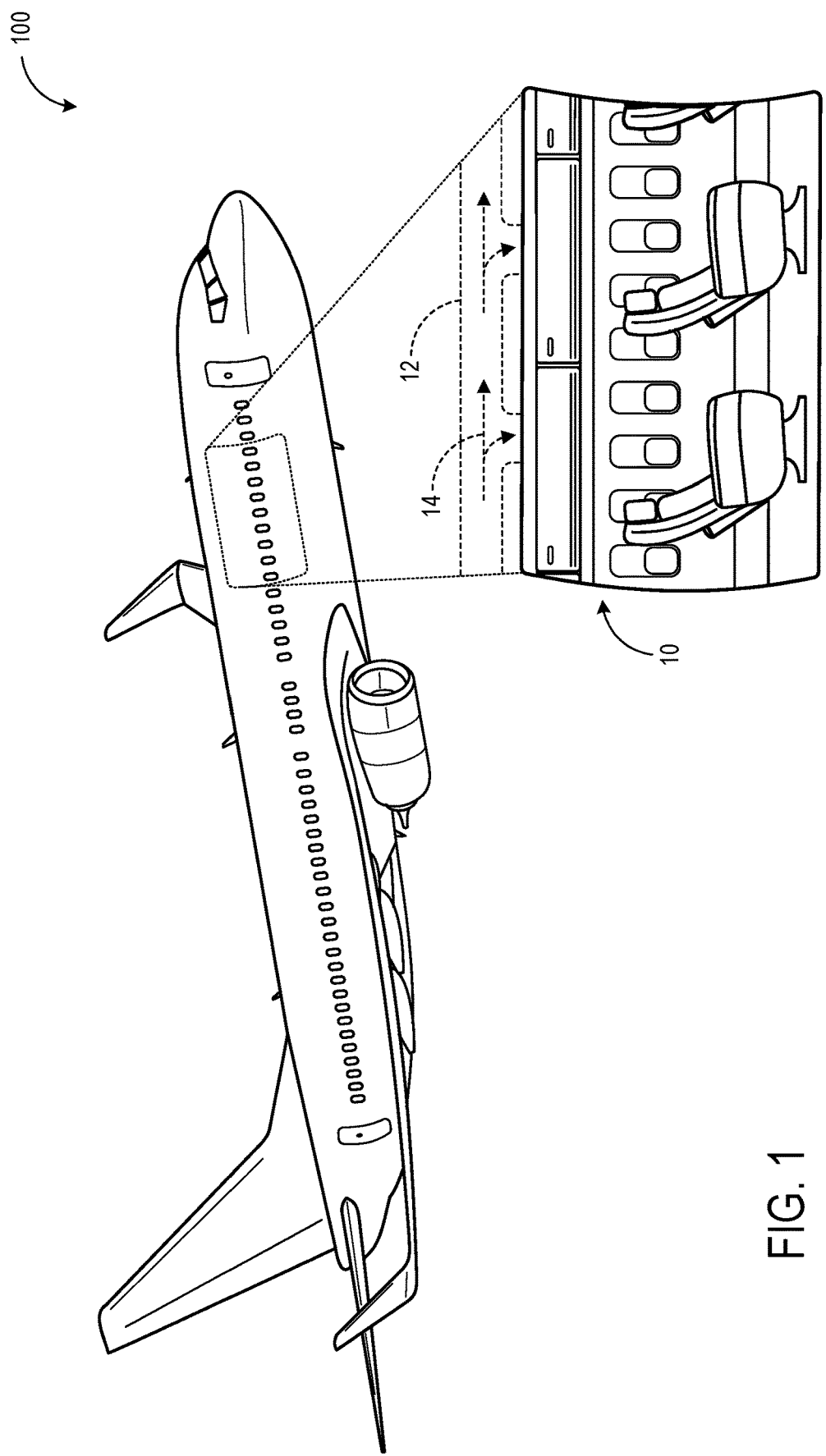
FIG. 1 shows an example aircraft, and illustrates airflow from a duct into a cabin according to the present disclosure.

Selected examples will now be explained with reference to the drawings, wherein like reference characters designate corresponding or identical elements throughout the various drawings. The following descriptions of the disclosed examples are provided for illustration only and not for the purpose of limiting the disclosure as defined by the appended claims and their equivalents.

FIG. 1 shows an aircraft 100, with a magnified view of a cabin 10 and an airflow passage 12 configured to confine a flow of air 14 and direct it toward the cabin 10. In many aircraft, at least a portion of the flow of air 14 in the airflow passage 12 input to the cabin 10 is recirculated from the cabin 10. A high efficiency particulate (HEPA) filter or the like may be placed in the airflow passage 12 to trap airborne pathogens and other particulates in the flow of air 14 is filtered before it is recirculated. However, HEPA filtration does not provide absolute sterilization, as this technology is not enabled for the destruction of pathogens. Additionally, HEPA filters can become clogged. Further, HEPA filters do not filter gaseous contaminants from the flow of air 14. As such, activated peroxide is promising for decontaminating air in occupied spaces. However, challenges exist in developing effective and efficient systems and methods for employing activated peroxide to treat contaminants in air.

Thus, examples are disclosed that relate to the use of peroxide-generating air purification elements to inactivate and destroy a variety of airborne contaminants, including pathogens and chemical contaminants.

Figure 2:
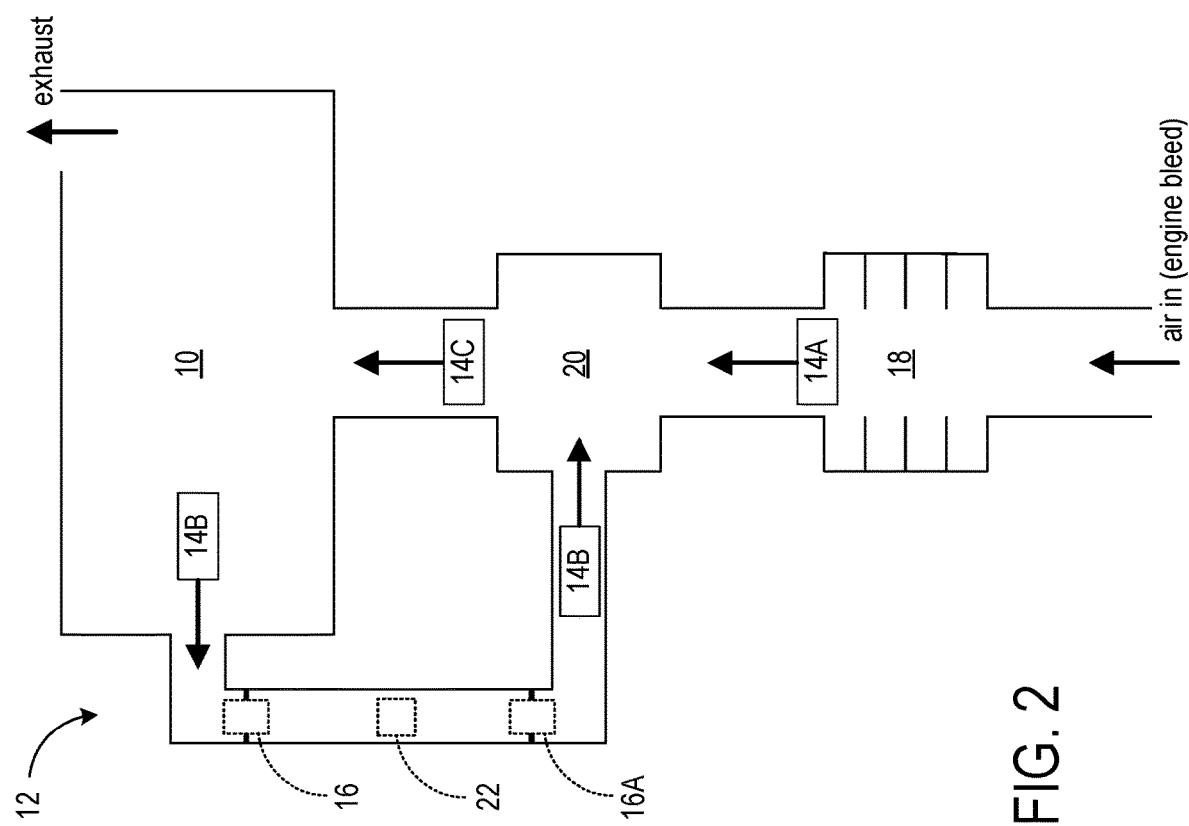
FIG. 2 shows a schematic diagram of an example airflow system for an aircraft with an air purification element positioned in an airflow passage, according to the present disclosure.

FIG. 2 shows a schematic diagram of the airflow passage 12 in the aircraft 100 with an air purification element 16 positioned in the airflow passage 12 according to the present disclosure. As described in detail below, the air purification element 16 is configured to produce a peroxide (e.g., hydrogen peroxide (11202)) to oxidize contaminants in the air 14 flowing through the airflow passage 12. The location of the air purification element 16 is optional, and an alternative or additional location for an air purification element is shown at 16A.

Typically, air in the cabin 10 is a mixture of air from an outside environment, such as engine bleed air, and air recirculated from the cabin 10. As illustrated, a flow of air 14A from the outside environment passes through an air conditioning pack 18, where it is compressed, cooled, and expanded, to a mixing manifold 20, where it is mixed with a flow of air 14B that is recirculated from the cabin 10. The flow of air 14B that is recirculated from the cabin 10 is extracted from the cabin 10, passes through the air purification element 16 and the HEPA filter 22. Additionally or alternatively to the air purification element 16, the flow of air 14B can pass through the air purification element 16A located downstream of the HEPA filter 22. The filtered and purified flow of air 14B from the cabin 10 then enters the mixing manifold 20 to be mixed with a flow of air 14A from the outside environment, and the resulting mixed flow of air 14C is directed into the cabin 10, thereby providing decontaminated air to passengers seated in the cabin 10 of the aircraft 100.

Figure 3:
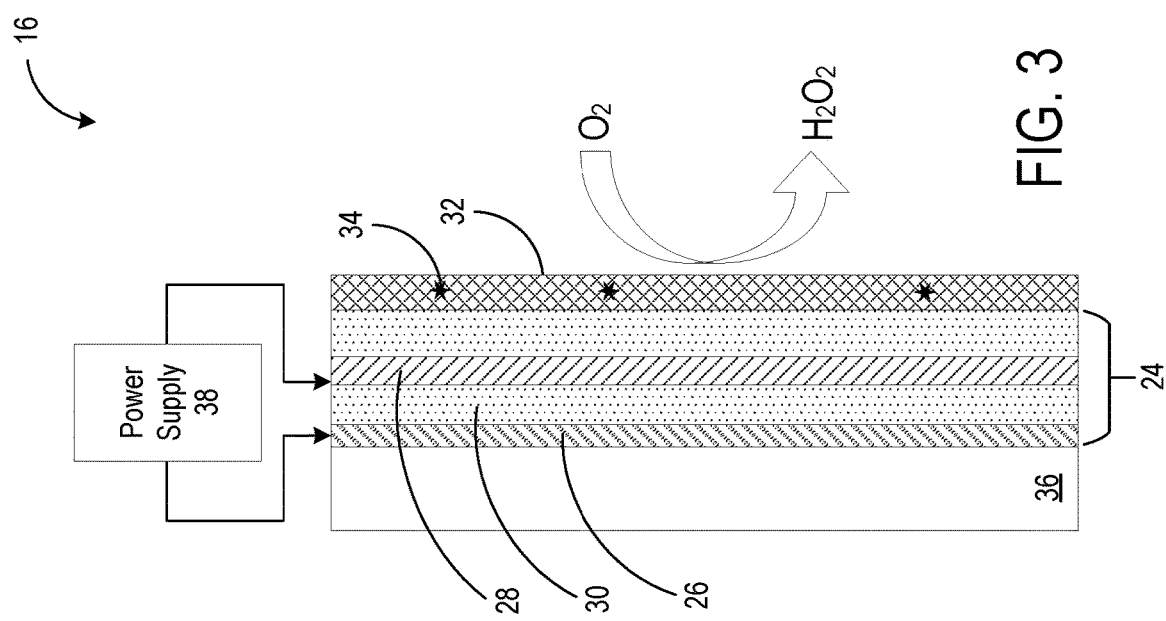
FIG. 3 shows a schematic diagram of an example air purification element according to the present disclosure.

FIG. 3 shows a schematic diagram of the air purification element 16. The air purification element 16 includes a peroxide-generating structure 24 comprising a first electrode 26 separated from a second electrode 28 by an ionically conductive matrix 30. The peroxide-generating structure 24 is configured to produce peroxide from water vapor and oxygen in flow of air 14 in the airflow passage 12 when energized by an energy source. The air purification element 16 further includes a matrix 32 (cross hatching) comprising a peroxide-activating catalyst 34 (schematically illustrated by stars) that is configured to activate the peroxide produced by lowering an activation energy for the peroxide to react with airborne contaminants. In some implementations, the air purification element 16 is constructed as layers on a base substrate 36, with the matrix 32 comprising the peroxide-activating catalyst 34 being an outermost layer from the substrate 36 so as to allow the contaminants to contact peroxide activated by the peroxide-activating catalyst 34. However, it will be appreciated that the peroxide-activating catalyst 34 can be alternatively positioned, such as distributed throughout the ionically conductive matrix 30.

In the example of FIG. 3, the air purification element 16 produces $H_2O_2$ upon the application of a voltage from a power supply 38 across the first electrode 26 and the second electrode 28. The first electrode 26 can be configured as an anode, and the second electrode 28 can be configured as a cathode. In the presence of a catalyst, e.g., $CaSnO_3$, $H_2O_2$ can be produced at the anode by the oxidation of the water vapor in the air 14 in the airflow passage 12. Additionally or alternatively, $H_2O_2$ can be produced at the cathode by the reduction of oxygen in the air 14. The produced peroxide then diffuses through the ionically conductive matrix 30 to the matrix 32 comprising the peroxide-activating catalyst 34. The peroxide-activating catalyst 34 can comprise, for example, complexes of ethylenediaminetetraacetic acid (EDTA) with metals such as iron, tetra-amido macrocyclic ligand (TAML®) complexes with metals such as iron, manganese gluconate, sodium hypochlorite, N-[4-(triethlyammoniomethyl)benzoyl]-caprolactam chloride, nonanoyloxybenzene sulfonate, porphyrins, phthalocyanines, ruthenium oxide, indium oxide, quinones, and the like, for example. The resulting activated peroxide can then migrate to the surface of the air purification element 16 where it contacts and oxidizes contaminants in the airflow passage 12. In some implementations, an electrocatalyst can be bound to the cathode to catalyze the formation of hydrogen ions. If desired, a hydrogen peroxide scavenger or a peroxide removal agent such as ascorbic acid can be provided in the airflow passage 12 downstream of the air purification element 16 to reduce or remove peroxide from the flow of air 14 before it is circulated back into an environment.

The air purification element can have any suitable configuration, based upon a desired end use. Example implementations of the air purification element 16 are described below with reference to FIGS. 4-11. In some implementations, the air purification element 16 can be configured as an integrated unit designed to be removably placed in the airflow passage 12. Additionally or alternatively, the air purification element 16 can be positioned in a housing configured to fit in the airflow passage 12. Further, the air purification element 16 can be configured to be replaceable (e.g. as a consumable item). The air purification element 16 can be configured in various ways and is adaptable for use in many environments, examples of which include aircraft, personal respiration devices, and habitable fixed structures (e.g. buildings such as hospitals, schools, offices, shopping centers, restaurants, public transportation vehicles, air conditioning units, and laboratories).

Figure 4:
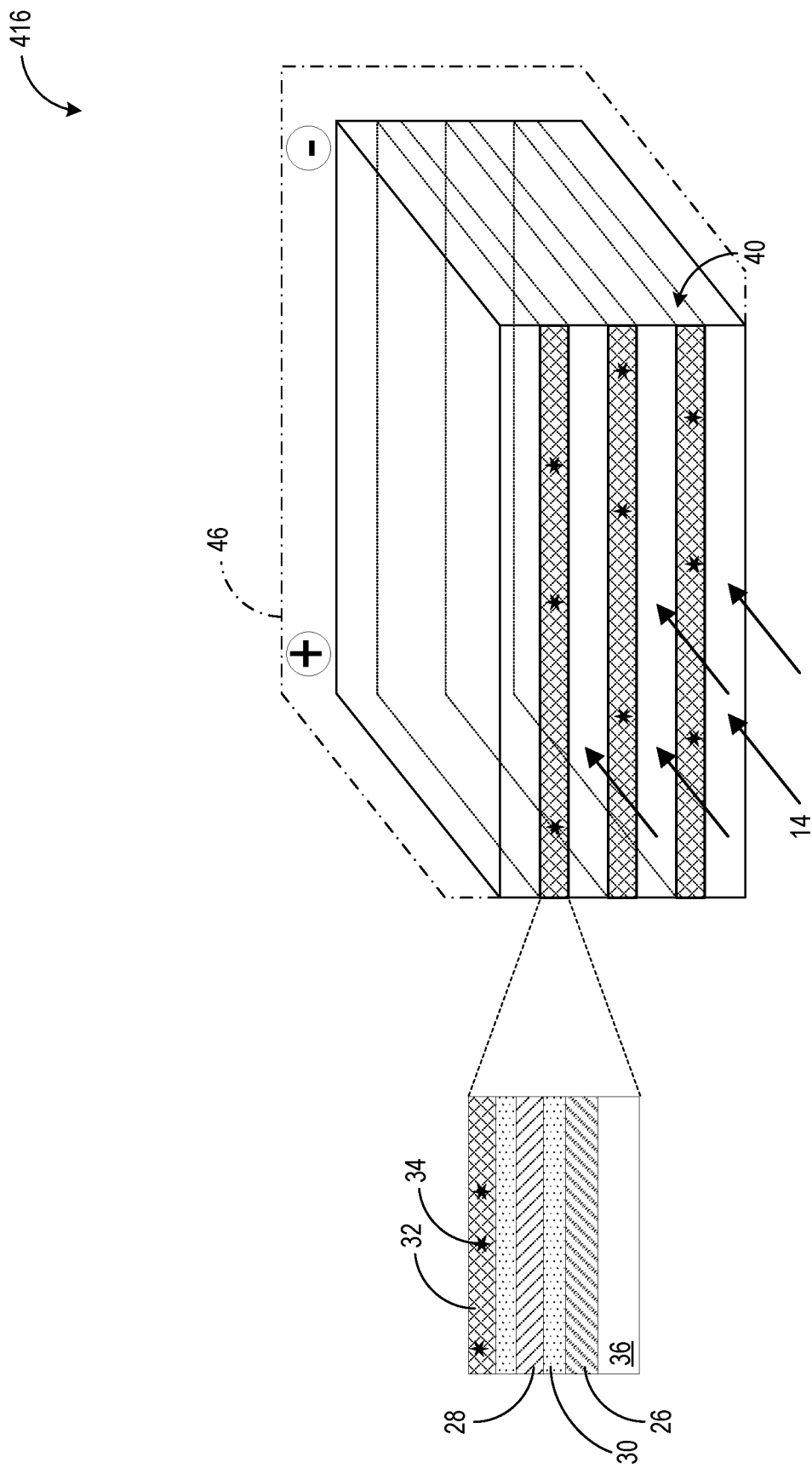
FIG. 4 schematically shows an example air purification element comprising a layered structure according to the present disclosure.

In the example of FIG. 4, the air purification element 16 is configured as an air purification element 416 that comprises a plurality of channels 40 through which an airflow can pass. The peroxide-generating structure 24 is located in each channel of the plurality of channels. In this implementation, each channel is formed by layering the individual layers of the peroxide-generating structure 24 on the base substrate 36, as described above with reference to FIG. 3, such that the matrix 32 with the peroxide-activating catalyst 34 is exposed to airflow within each channel 40. The channels 40 can be arranged horizontally, as shown in FIG. 4, vertically or diagonally, or in any other suitable orientation with respect to an airflow passage in which they are used. As the flow of air 14 is directed through the airflow passage 12, contaminants in the air contact activated peroxide at the surface of the air purification element 416 and are oxidized. While the channels 40 are shown comprise a rectangular cross-section, the channels 40 can have any other suitable shape, and the shape can vary along a direction of airflow. In some examples, the channels 40 are contained within a removable unit (e.g. a housing) configured to be placed within another airflow passage. In such examples, the housing 46 can comprise electrical contacts (+, −) configured to contact complementary electrical contacts in an airflow passage. In other examples, the housing can be configured to hold one or more batteries (not shown) as a power supply.

Figure 6:
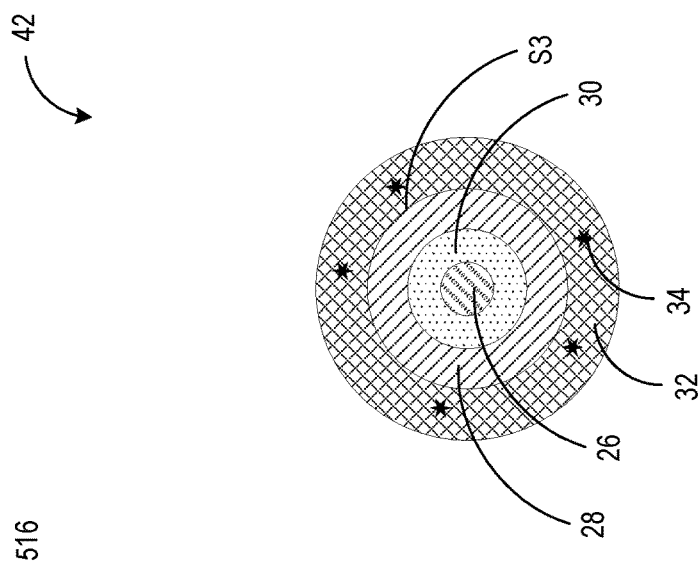
FIG. 6 shows a sectional view of an example peroxide-generating structure configured as a rod according to the present disclosure.
Figure 5:
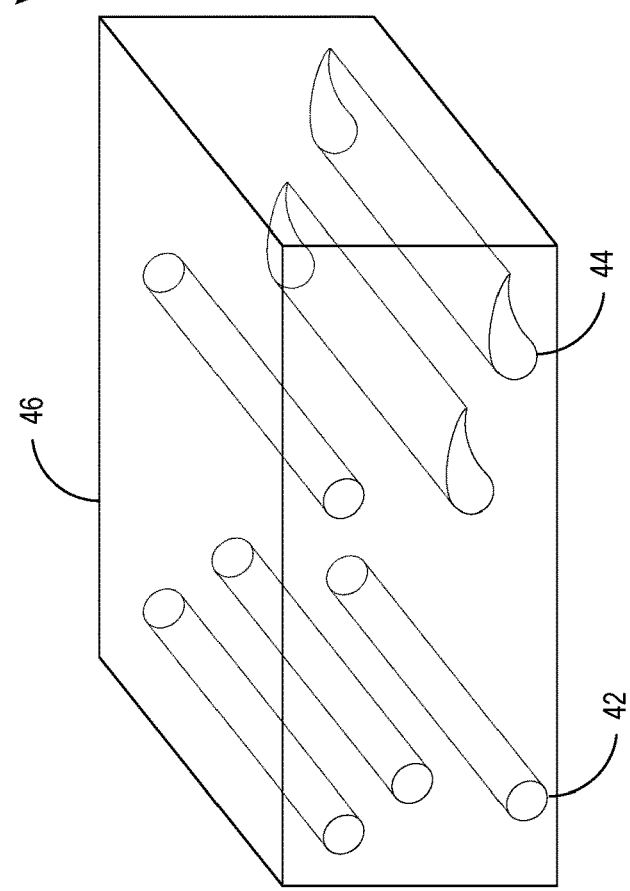
FIG. 5 shows an example air purification element comprising peroxide-generating structures configured as rods according to the present disclosure.

FIGS. 5 and 6 show the air purification element 16 configured as an example air purification element 516 in which peroxide-generating structure 24 is configured as rod-shaped structures 42 and vane-shaped structures 44. In this configuration, as shown in the sectional view of the rod-shaped structure 40 in FIG. 6, the first electrode 26 is at least partially surrounded by the second electrode 28. The ionically conductive matrix 30 is disposed therebetween, and the matrix 32 containing the peroxide-activating catalyst 34 is arranged on an outer surface (S3) of the second electrode 28. A plurality of rod- and/or vane-shaped structures 42, 44 can be arranged in a housing 46 that is configured to be removably inserted into the airflow passage 12. When the flow of air 14 is directed through the airflow passage 12, contaminants in the air contact activated peroxide at the surface of the air purification element 16 and are destroyed via oxidation. The housing 46 can include a battery compartment and/or electrical contacts for connecting to a power supply, as described above with regard to FIG. 4.

Figure 7:
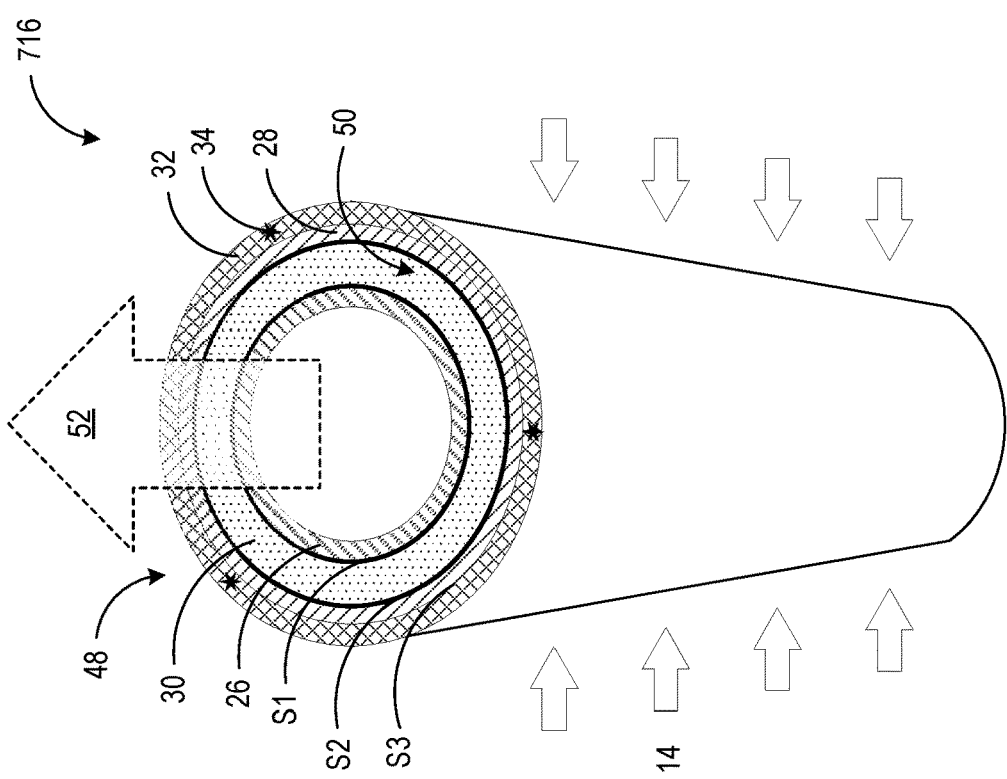
FIG. 7 shows an example air purification element configured as a hollow fiber of a porous material according to the present disclosure.

FIG. 7 shows the air purification element 16 configured as an air purification element 716. In this example, an air purification element 716 comprises a hollow fiber 48 of a porous material 50. The first electrode 26 positioned on a first surface 51 of the hollow fiber 48 (here shown as an inner surface), the second electrode 28 is positioned on a second surface S2 of the hollow fiber 48, and the ionically conductive matrix 30 is positioned in the porous material 50 between the first and second electrodes 26, 28. The matrix 32 containing the peroxide-activating catalyst 34 is arranged on an outer surface (S3) of the second electrode 28 so as to be exposed to the flow of air 14 in the airflow passage 12. One or more hollow fibers 48 can be positioned in the airflow passage 12 such that contaminants in the air 14 flowing through the airflow passage 12 contact the activated peroxide at the surface of the air purification element 716 and are oxidized. In this configuration, purified air 52 flows out from the center of the hollow fiber 48, as shown in FIG. 7.

Figure 8:
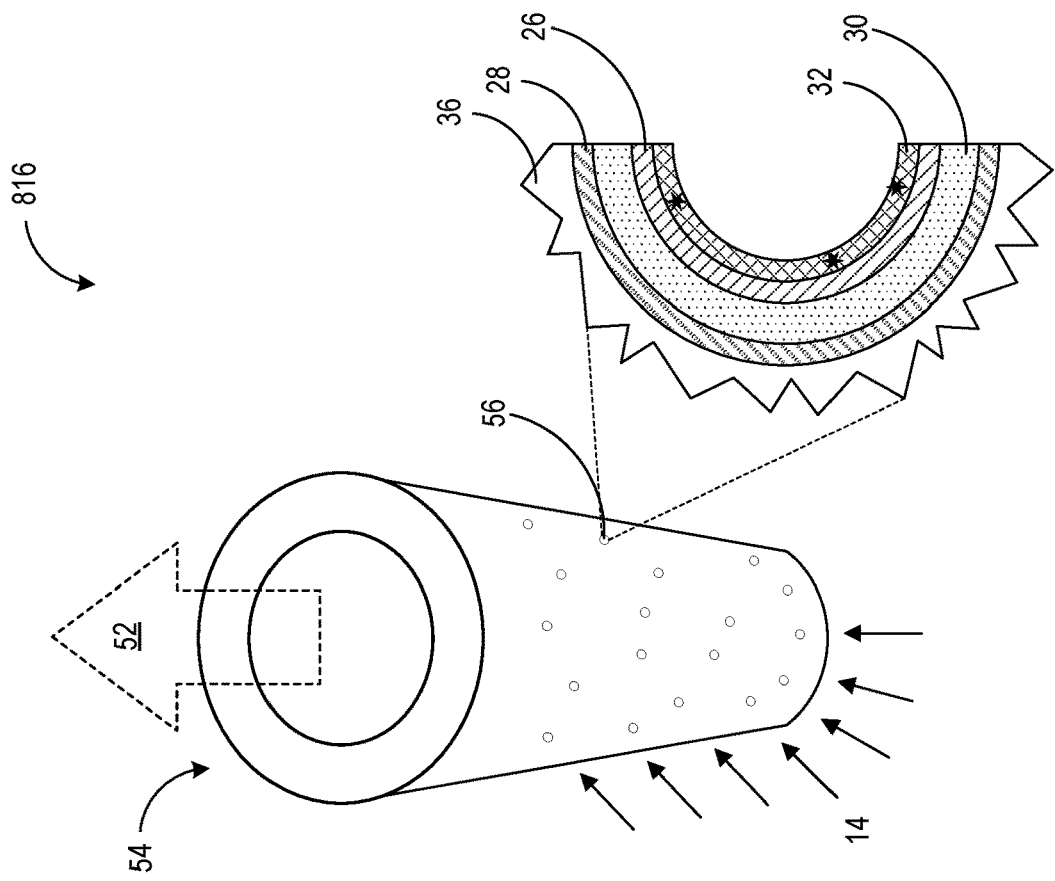
FIG. 8 shows an example air purification element configured as a hollow fiber comprising a plurality of pores according to the present disclosure.

FIG. 8 shows the air purification element 16 is configured as an air purification element 816 that comprises a hollow fiber 54 of a porous material 55 that includes a plurality of pores 56. As illustrated schematically in the magnified view of FIG. 8, in each of one or more pores 56 of the plurality of pores 56, the peroxide-generating structure 24 comprises a layered structure built on the substrate 36, with the first and second electrodes 26, 28 separated by the ionically conductive matrix 30. The matrix 32 containing the peroxide-activating catalyst 34 arranged on an outer surface (S3) of the second electrode 28. Similar to the implementation of the hollow fiber 48 described above with reference to FIG. 7, one or more hollow fibers 54 can be positioned in the airflow passage 12 such that contaminants in the air 14 flowing through the airflow passage 12 can contact the activated peroxide at the surface of the air purification element 816 and be oxidized. Purified air 52 flows out from the center of the hollow fiber 54.

Figure 9:
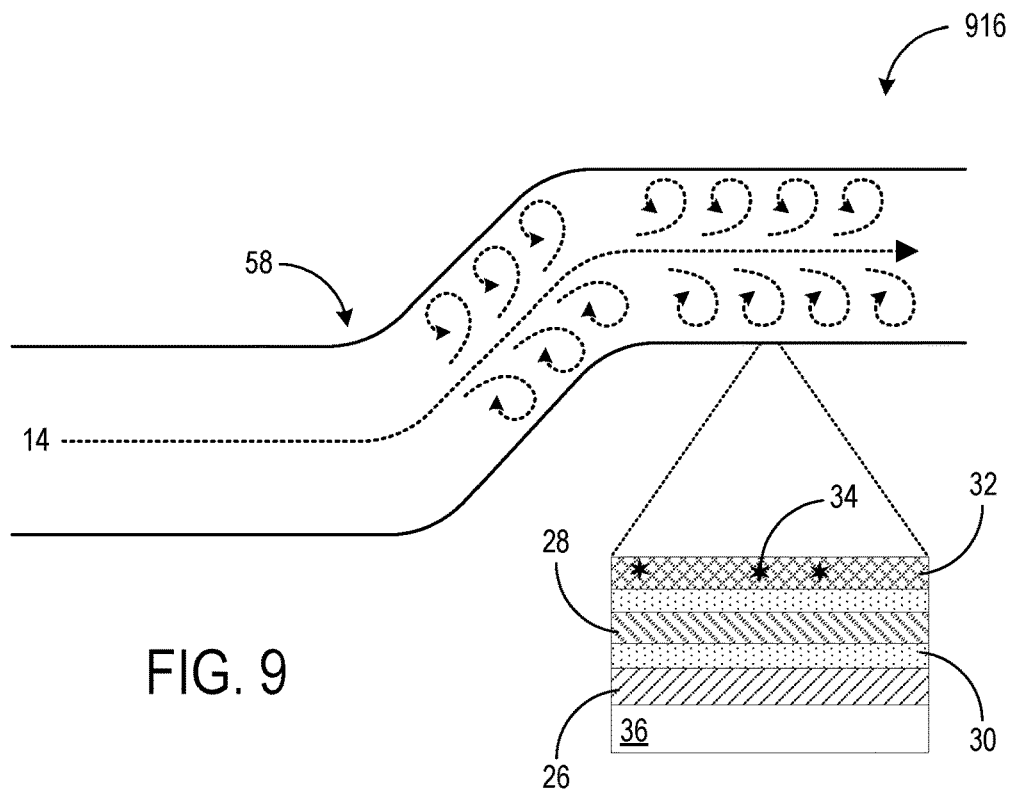
FIG. 9 shows an air purification element configured as a curved airflow channel according to the present disclosure.
Figure 10:
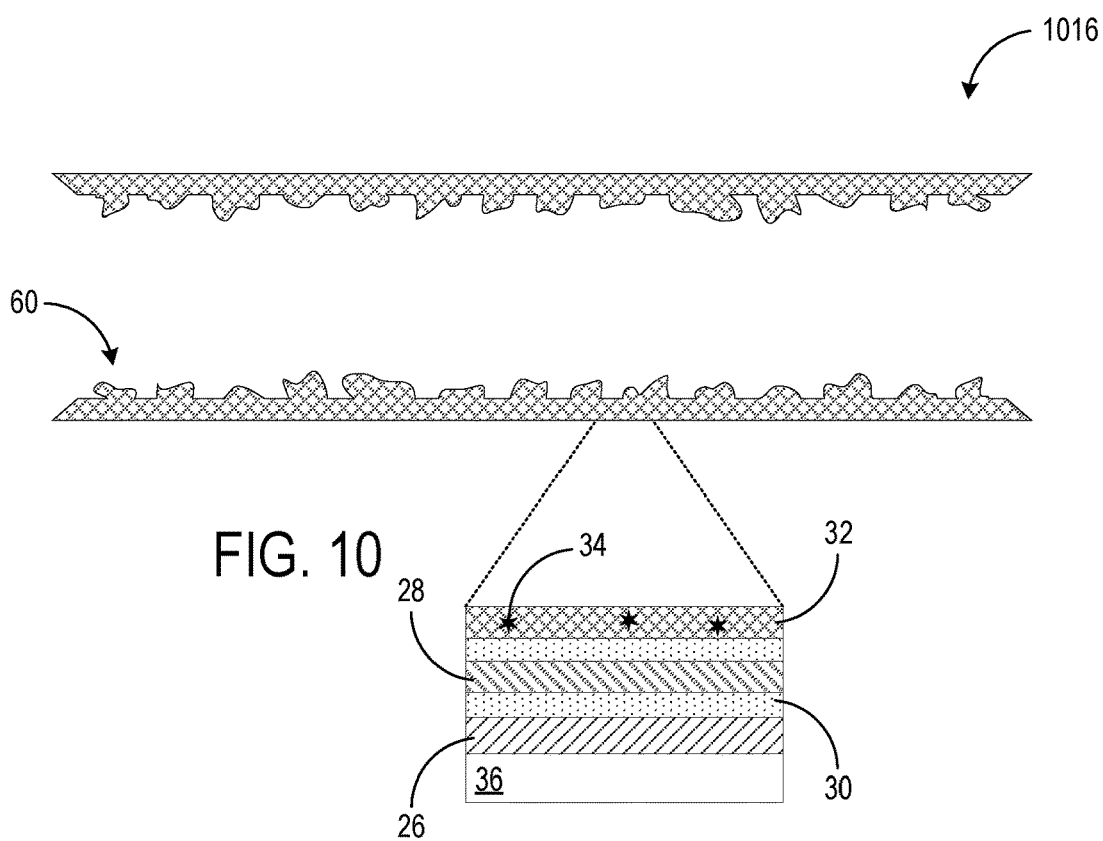
FIG. 10 shows an air purification element configured as a textured airflow channel according to the present disclosure.
Figure 11:
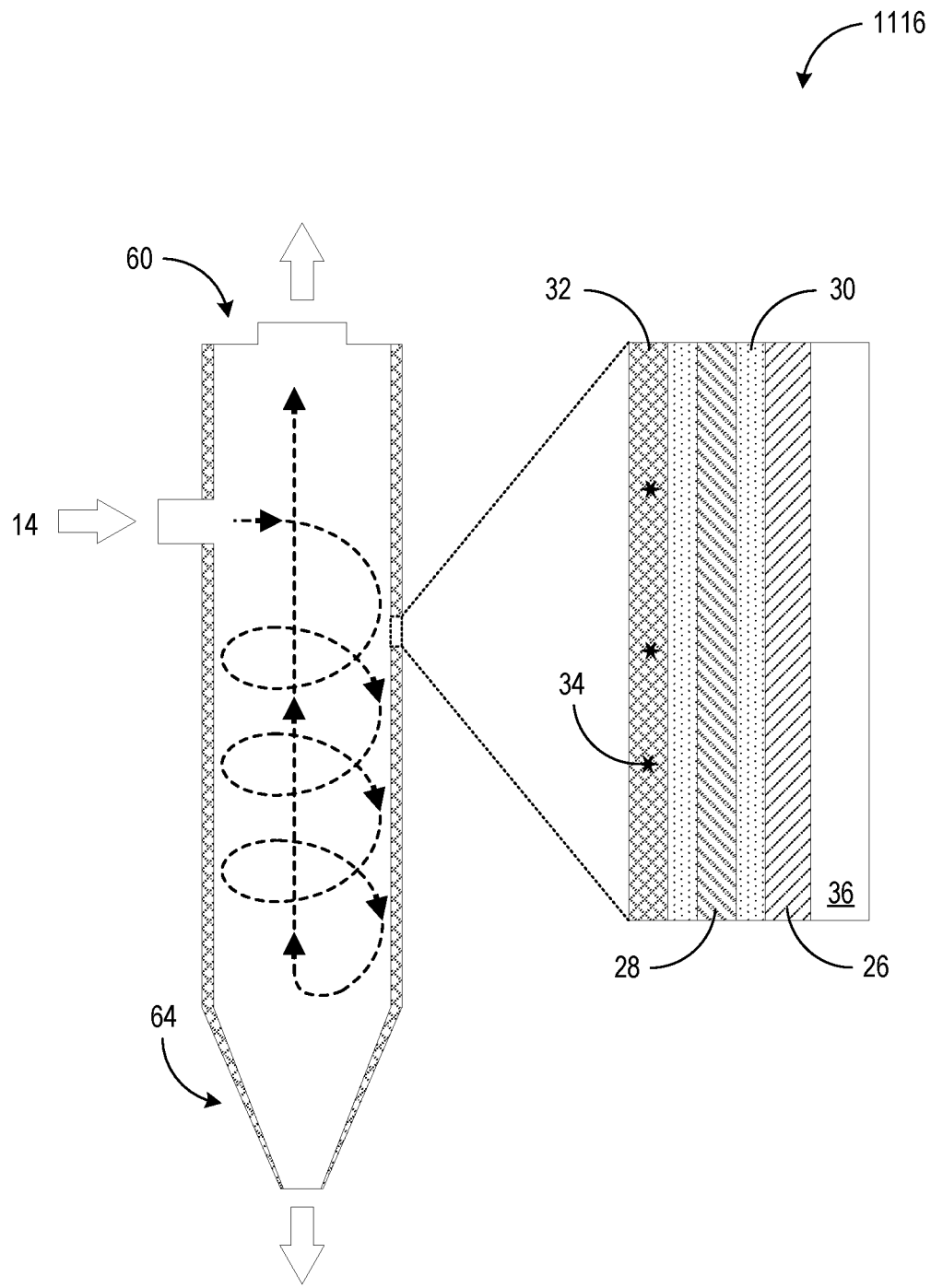
FIG. 11 shows an air purification element configured as a channel that creates a vortex according to the present disclosure.

In some implementations, a channel in an air purification element can have a configuration that helps to achieve turbulent flow so that air in a center of the channel flows toward the surface(s) of the channel and is exposed to activated peroxide. FIGS. 9-11 show examples of such structures. First, FIG. 9 shows the air purification element 16 configured as an air purification element 916 comprising a curved airflow channel 58 to create turbulent airflow. FIG. 10 shows the air purification element 16 configured as an air purification element 1016 comprising a surface 60 having a texture to create turbulent airflow. Channel 58 and surface 60 can be used, for example, in the layered air purification element of FIG. 4. In FIG. 11, the air purification element 16 is configured as an air purification element 1116 that comprises a channel 62 having a tapered end 64 configured to create a vortex in airflow through the channel 62. As illustrated in the magnified views of the curved airflow channel 58 of FIG. 9, the textured surface 60 of FIG. 10, and the channel 62 of FIG. 11, the peroxide-generating structure 24 is formed on the substrate 36 and overlaid with the matrix 32 comprising the peroxide-activating catalyst 34 such that contaminants in the flow of air 14 contact the activated peroxide and are oxidized.

Figures 12, 13:
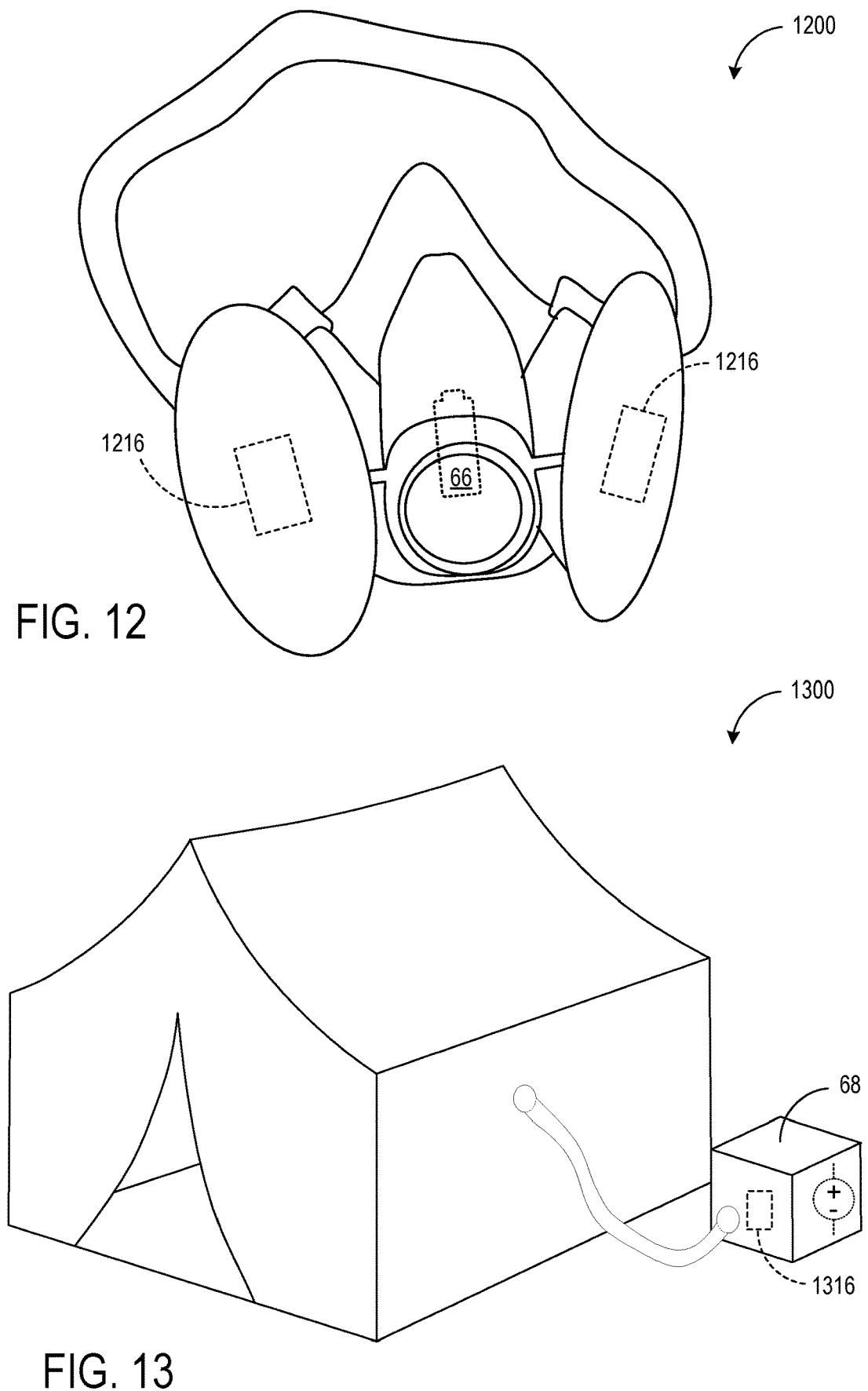
FIG. 12 shows an air purification element in a personal respiration device according to the present disclosure.
FIG. 13 shows an air purification element in a habitable fixed structure according to the present disclosure.

In some use-case scenarios, such as biomedical or military applications in which a user may be exposed to airborne pathogens and/or toxins, it can be desirable to include an air purification element in personal protective equipment (PPE), such as a mask, to provide the user with decontaminated air. FIG. 12 shows the air purification element 16 configured as an example air purification element 1216 in a personal respiration device 1200. In this implementation, the air purification element 1216 can be enclosed in a housing that is configured to be coupled with the personal respiration device 1200. The personal respiration device 1200 can be reusable or disposable. When the personal respiration device 1200 is designed to be disposable, the air purification element 1216 preferably comprises a battery 66. When implemented as the battery 66, the first electrode 26 can be configured as an anode comprising sacrificial zinc or silver that is oxidized, and the second electrode 28 can be configured as a carbon cathode that reduces oxygen to form peroxide.

While the personal respiration device 1200 is illustrated as a half mask respirator, it will be appreciated that the personal respiration device 1200 can be configured as any other suitable type of personal respiration device, such as a full mask respirator, a powered air-purifying respirator (PAPR), a supplied air respirator (SAR), a self-contained breathing apparatus (SOBA), gas masks, and the like, for example. Additionally or alternatively, the air purification element 16 can be inserted in cartridges or cannisters that are used in conjunction with a personal respiration device.

Some emergency situations require rapid deployment of semi-permanent biomedical or military structures in potentially hazardous conditions or conversion of existing permanent structures for emergency use. Such situations include management of a biohazard event, containment of an outbreak, isolation and medical treatment of persons infected with a highly contagious pathogen, and military installation in an area in which biological warfare agents may be used, for example. Accordingly, FIG. 13 shows the air purification element 16 configured as an air purification element 1316 designed for use with a habitable fixed structure 1300. In this implementation, the air purification element 1316 can be enclosed in an air conditioning unit 68 positioned outside of the habitable fixed structure 1300 and configured to deliver decontaminated, conditioned air to the habitable fixed structure 1300. The air purification element 1316 can be enclosed in a housing and can comprise electrical contacts configured to engage with a power supply included in the air conditioning unit. While the habitable fixed structure 1300 in FIG. 13 is illustrated as a tent, it will be appreciated that the habitable fixed structure 1300 can be configured as a hangar, trailer, barracks, school, office building, hospital, community center, recreational facility, or any other suitable structure.

Figure 14:
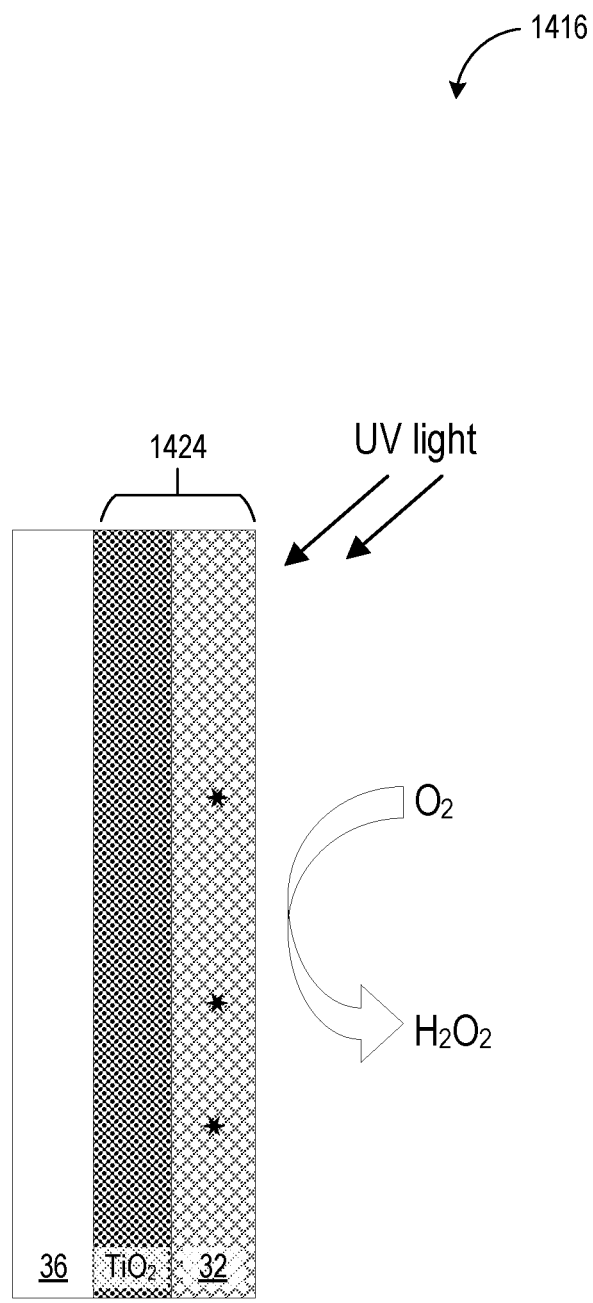
FIG. 14 shows an example air purification element utilizing ultraviolet light to energize a peroxide-generating structure according to the present disclosure.

In other examples, instead of an electrochemical peroxide generator, a photochemical peroxide generator mechanism can be used. For example, the photochemical oxidation of titanium dioxide ($TiO_2$) or other heterogeneous photocatalysts such as ferric oxide ($Fe_2O_3$) or zinc oxide (ZnO) with ultraviolet (UV) light in the presence of water and oxygen can produce $H_2O_2$. To this end, FIG. 14 shows the air purification element 16 configured as an air purification element 1416 in which the peroxide-generating structure 24 is configurated as a peroxide-generating structure 1424 that comprises a photochemical peroxide generator. When the peroxide-generating structure 1424 is illuminated with UV light in the presence of water vapor and oxygen in the air flow passage 12, $H_2O_2$ is generated. Like the air purification element 16 described above with reference to FIG. 3, the photochemical air purification element 1416 can include a matrix 32 comprising the peroxide-activating catalyst 34 that is configured to activate the peroxide. In some examples, the peroxide-activating catalyst 34 comprises TAML®. In other examples, the peroxide-activating catalyst 34 can comprise any other suitable complex or compound, such as those discussed above with reference to FIG. 3.

Figure 15:
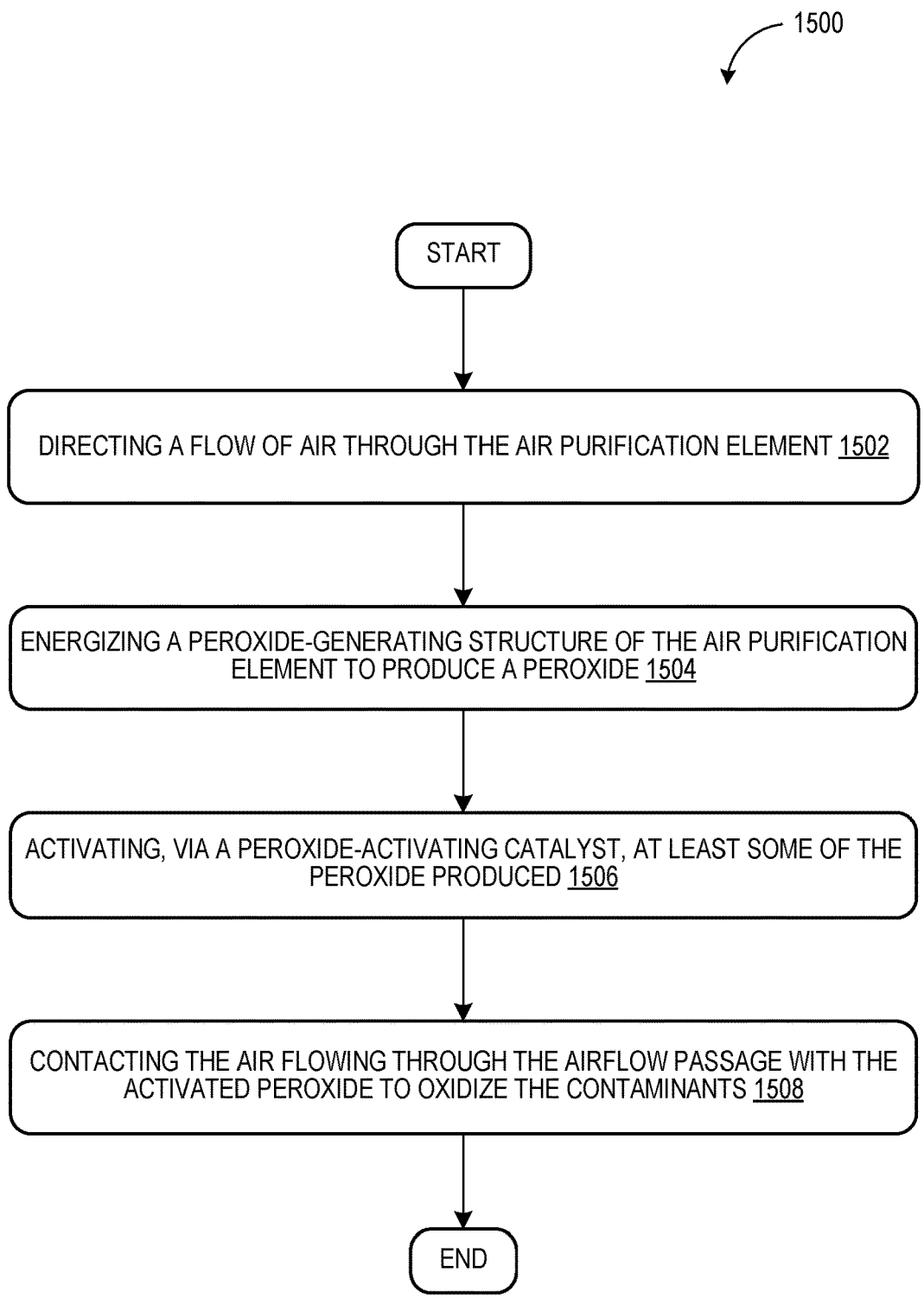
FIG. 15 is a flow diagram illustrating an example method of oxidizing contaminants in air via an air purification element according to the present disclosure.

FIG. 15 is a flow diagram showing an example method 1500 of oxidizing contaminants in air flowing through an airflow passage. The method 1500 is an efficient and effective way to purify air of airborne contaminants via oxidation. The following description of method 1500 is provided with reference to the air purification element 16 described above and shown in FIG. 3, with exemplary embodiments shown in FIGS. 4-11. It will be appreciated that method 1500 can also be performed in other contexts using other suitable components.

With reference to FIG. 15, at 1502, the method 1500 includes directing a flow of air through the air purification element. At 1504, the method 1500 includes energizing a peroxide-generating structure of the air purification element to produce a peroxide from water vapor and oxygen in the airflow passage. In some examples, the peroxide-generating structure can be energized via an applied electrical potential, while in other examples the peroxide-generating structure can be energized via incident light. At 1506, the method 1500 includes activating, via a peroxide-activating catalyst, at least some of the peroxide produced. At 1508, the method 1500 includes contacting the air flowing through the airflow passage with the peroxide activated to oxidize contaminants.

The following paragraphs provide additional support for the claims of the subject application. One aspect provides a system comprising an airflow passage and an air purification element positioned in the airflow passage. The airflow passage is configured to confine a flow of air and direct the flow of air toward a space, and the air purification element is configured to produce a peroxide to oxidize contaminants in air flowing through the airflow passage. The air purification element includes a peroxide-generating structure and a matrix containing a peroxide-activating catalyst. The peroxide-generating structure is configured to produce the peroxide from a water vapor and oxygen in the air within the airflow passage when energized by an energy source, and the matrix containing the peroxide-activating catalyst is configured to activate the peroxide produced and allow the contaminants to contact peroxide activated by the peroxide-activating catalyst. In this aspect, additionally or alternatively, the peroxide-generating structure comprises an electrode pair separated by an ionically conductive matrix, and an electrocatalyst. In this aspect, additionally or alternatively, the peroxide-generating structure comprises titanium dioxide. In this aspect, additionally or alternatively, the system comprises an aircraft, and the airflow passage in which the air purification element is positioned is configured to provide air to a cabin of the aircraft.

In this aspect, additionally or alternatively, the system comprises a personal respiration device. In this aspect, additionally or alternatively, the system comprises a habitable fixed structure. In this aspect, additionally or alternatively, the air purification element comprises an integrated unit configured to be removably placed in the airflow passage. In this aspect, additionally or alternatively, the air purification element comprises a plurality of channels for airflow, and the peroxide-generating structure and the peroxide-activating catalyst are located in each channel of the plurality of channels. In this aspect, additionally or alternatively, the air purification element comprises a surface having a texture to create turbulent airflow. In this aspect, additionally or alternatively, the air purification element comprises a curved airflow channel to create turbulent airflow. In this aspect, additionally or alternatively, the air purification element comprises a hollow fiber of a porous material; the peroxide-generating structure comprises a first electrode positioned on a first surface of the hollow fiber, a second electrode positioned on a second surface of the hollow fiber, and an ionically conductive matrix positioned between the first electrode and the second electrode in the porous material; and the matrix containing the peroxide-activating catalyst is arranged on a surface of the second electrode. In this aspect, additionally or alternatively, the air purification element comprises a hollow fiber of a porous material comprising a plurality of pores, and the peroxide-generating structure comprises, in each of one or more pores of the plurality of pores, a first electrode and a second electrode separated by an ionically conductive matrix. The matrix containing the peroxide-activating catalyst is arranged on an outer surface of the second electrode. In this aspect, additionally or alternatively, the air purification element comprises a channel configured to create a vortex in airflow through the channel. In this aspect, additionally or alternatively, the peroxide-generating structure comprises one or more of a rod-shaped structure and a vane-shaped structure having a first electrode at least partially surrounded by a second electrode with an ionically conductive matrix disposed therebetween, and the matrix containing the peroxide-activating catalyst is arranged on a surface of the second electrode.

Another aspect provides an aircraft comprising a cabin, an airflow passage, and an air purification element positioned in the airflow passage. The airflow passage is configured to confine a flow of air and direct the flow of air toward a space, and the air purification element is configured to produce a peroxide to oxidize contaminants in air flowing through the airflow passage. The air purification element includes a peroxide-generating structure and a matrix containing a peroxide-activating catalyst. The peroxide-generating structure is configured to produce the peroxide from a water vapor and oxygen in the air within the airflow passage. The peroxide-generating structure includes a first electrode separated from a second electrode by an ionically conductive matrix and is configured to produce the peroxide upon application of a voltage across the first electrode and the second electrode. The matrix containing the peroxide-activating catalyst is configured to activate the peroxide produced and is positioned to allow the contaminants to contact peroxide activated by the peroxide-activating catalyst.

Another aspect provides a method of oxidizing contaminants in air flowing through an airflow passage via an air purification element. The method comprises directing a flow of air through the air purification element, energizing a peroxide-generating structure of the air purification element to produce a peroxide from water vapor and oxygen in the airflow passage, activating, via a peroxide-activating catalyst, at least some of the peroxide produced, and contacting the air flowing through the airflow passage with the activated peroxide to oxidize the contaminants. In this aspect, additionally or alternatively, energizing the peroxide-generating structure comprises applying a voltage across a pair of electrodes, and generating peroxide via an electrocatalyst. In this aspect, additionally or alternatively, energizing the peroxide-generating structure comprises illuminating the peroxide-generating structure with ultraviolet light. In this aspect, additionally or alternatively, directing the flow of air through the air purification element comprises creating a vortex in the air flowing through the airflow passage. In this aspect, additionally or alternatively, directing the flow of air through the air purification element comprises flowing the air through a plurality of airflow channels in the air purification element. In this aspect, additionally or alternatively, directing the flow of air through the air purification element comprises flowing the air through one or more hollow porous fibers.

Another aspect provides a replaceable air purification element. The replaceable air purification element comprises a housing, a peroxide-generating structure, and a matrix containing a peroxide-activating catalyst. The housing is configured to be removably inserted into an airflow passage that confines a flow of air and directs the flow of air toward a space. The peroxide-generating structure is positioned within the housing and is configured to produce a peroxide from a water vapor and oxygen in the air within the airflow passage when energized by an energy source. The matrix containing a peroxide-activating catalyst is configured to activate the peroxide produced and allow contaminants in the flow of air to contact peroxide activated by the peroxide-activating catalyst. In this aspect, additionally or alternatively, the peroxide-generating structure comprises a pair of electrodes separated by an ionically conductive matrix and an electrocatalyst, and the replaceable air purification element further comprises electrical contacts. In this aspect, additionally or alternatively, the peroxide-generating structure comprises titanium dioxide. In this aspect, additionally or alternatively, the housing is configured to fit within an airflow passage of an aircraft. In this aspect, additionally or alternatively, the housing is configured to be coupled with a personal respiration device. In this aspect, additionally or alternatively, the air purification element comprises a plurality of channels for airflow, and the peroxide-generating structure and the peroxide-activating catalyst are located in each channel of the plurality of channels. In this aspect, additionally or alternatively, the air purification element comprises a surface having a texture to create turbulent airflow. In this aspect, additionally or alternatively, the air purification element comprises a curved airflow channel to create turbulent airflow. In this aspect, additionally or alternatively, the air purification element comprises a hollow fiber of a porous material. In this aspect, additionally or alternatively, the air purification element comprises a channel having a tapered end configured to create a vortex in airflow through the channel. In this aspect, additionally or alternatively, the peroxide-generating structure comprises one or more of a rod-shaped structure and a vane-shaped structure having a first electrode at least partially surrounded by a second electrode with an ionically conductive matrix disposed therebetween. In this aspect, additionally or alternatively, the peroxide-generating structure comprises a battery.

Further, the disclosure comprises examples according to the following clauses:

Clause 1. A system, comprising: an airflow passage configured to confine a flow of air and direct the flow of air toward a space; and an air purification element positioned in the airflow passage and configured to produce a peroxide to oxidize contaminants in air flowing through the airflow passage, the air purification element including: a peroxide-generating structure configured to produce the peroxide from a water vapor and oxygen in the air within the airflow passage when energized by an energy source; and a matrix containing a peroxide-activating catalyst configured to activate peroxide produced, the matrix being configured to allow the contaminants to contact peroxide activated by the peroxide-activating catalyst.

Clause 2. The system of Clause 1, wherein the peroxide-generating structure comprises an electrode pair separated by an ionically conductive matrix, and an electrocatalyst.

Clause 3. The system of Clause 1 or 2, wherein the peroxide-generating structure comprises titanium dioxide.

Clause 4. The system of any of Clauses 1 to 3, wherein the system comprises an aircraft, and the airflow passage in which the air purification element is positioned is configured to provide air to a cabin of the aircraft.

Clause 5. The system of any of Clauses 1 to 3, wherein the system comprises a personal respiration device.

Clause 6. The system of any of Clauses 1 to 3, wherein the system comprises a habitable fixed structure.

Clause 7. The system of any of Clauses 1 to 6, wherein the air purification element comprises an integrated unit configured to be removably placed in the airflow passage.

Clause 8. The system of any of Clauses 1 to 7, wherein the air purification element comprises a plurality of channels for airflow, and the peroxide-generating structure and the peroxide-activating catalyst are located in each channel of the plurality of channels.

Clause 9. The system of any of Clauses 1 to 8, wherein the air purification element comprises a surface having a texture to create turbulent airflow.

Clause 10. The system of any of Clauses 1 to 9, wherein the air purification element comprises a curved airflow channel to create turbulent airflow.

Clause 11. The system of any of Clauses 1 to 7, wherein the air purification element comprises a hollow fiber of a porous material; and the peroxide-generating structure comprises a first electrode positioned on a first surface of the hollow fiber, a second electrode positioned on a second surface of the hollow fiber, and an ionically conductive matrix positioned between the first electrode and the second electrode in the porous material, wherein the matrix containing the peroxide-activating catalyst is arranged on an outer surface of the second electrode.

Clause 12. The system of any of Clauses 1 to 7, wherein the air purification element comprises a hollow fiber of a porous material comprising a plurality of pores, the peroxide-generating structure comprises, in each of one or more pores of the plurality of pores, a first electrode and a second electrode separated by an ionically conductive matrix, and the matrix containing the peroxide-activating catalyst is arranged on an outer surface of the second electrode.

Clause 13. The system of any of Clauses 1 to 7 and 9, wherein the air purification element comprises a channel configured to create a vortex in airflow through the channel.

Clause 14. The system of any of Clauses 1 to 7, wherein the peroxide-generating structure comprises one or more of a rod-shaped structure and a vane-shaped structure having a first electrode at least partially surrounded by a second electrode with an ionically conductive matrix disposed therebetween, and the matrix containing the peroxide-activating catalyst is arranged on an outer surface of the second electrode.

Clause 15. An aircraft, comprising: a cabin; an airflow passage configured to confine a flow of air and direct the flow of air toward the cabin; and an air purification element positioned in the airflow passage and configured to produce a peroxide to oxidize contaminants in air flowing through the airflow passage, the air purification element including: a peroxide-generating structure configured to produce the peroxide from water vapor and oxygen in the airflow passage, the peroxide-generating structure including a first electrode separated from a second electrode by an ionically conductive matrix and being configured to produce the peroxide upon application of a voltage across the first electrode and the second electrode; and a matrix containing a peroxide-activating catalyst configured to activate the peroxide produced, the matrix containing the peroxide-activating catalyst being positioned to allow the contaminants to contact peroxide activated by the peroxide-activating catalyst.

Clause 16. A method of oxidizing contaminants in air flowing through an airflow passage via an air purification element, the method comprising: directing a flow of air through the air purification element; energizing a peroxide-generating structure of the air purification element to produce a peroxide from water vapor and oxygen in the airflow passage; activating, via a peroxide-activating catalyst, at least some of the peroxide produced; and contacting the air flowing through the airflow passage with the activated peroxide to oxidize the contaminants.

Clause 17. The method of Clause 16, wherein energizing the peroxide-generating structure comprises applying a voltage across a pair of electrodes, and generating peroxide via an electrocatalyst.

Clause 18. The method of Clause 16, wherein energizing the peroxide-generating structure comprises illuminating the peroxide-generating structure with ultraviolet light.

Clause 19. The method of any of Clauses 16 to 18, wherein directing the flow of air through the air purification element comprises creating a vortex in the air flowing through the airflow passage.

Clause 20. The method of any of Clauses 16 to 18, wherein directing the flow of air through the air purification element comprises flowing the air through a plurality of airflow channels in the air purification element.

Clause 21. The method of any of Clauses 16 to 18, wherein directing the flow of air through the air purification element comprises flowing the air through one or more hollow porous fibers.

Clause 22. A replaceable air purification element, comprising: a housing configured to be removably inserted into an airflow passage that confines a flow of air and directs the flow of air toward a space; a peroxide-generating structure positioned within the housing, the peroxide-generating structure configured to produce a peroxide from a water vapor and oxygen in the air within the airflow passage when energized by an energy source; and a matrix containing a peroxide-activating catalyst configured to activate the peroxide produced, the matrix containing the peroxide-activating catalyst being configured to allow contaminants in the flow of air to contact peroxide activated by the peroxide-activating catalyst.

Clause 23. The replaceable air purification element of Clause 22, wherein the peroxide-generating structure comprises a pair of electrodes separated by an ionically conductive matrix and an electrocatalyst, and the replaceable air purification element further comprises electrical contacts.

Clause 24. The replaceable air purification element of Clause 22 or 23, wherein the peroxide-generating structure comprises titanium dioxide.

Clause 25. The replaceable air purification element of any of Clauses 22 to 24, wherein the housing is configured to fit within an airflow passage of an aircraft.

Clause 26. The replaceable air purification element of any of Clauses 22 to 24, wherein the housing is configured to be coupled with a personal respiration device.

Clause 27. The replaceable air purification element of any of Clauses 22 to 26, wherein the air purification element comprises a plurality of channels for airflow, and the peroxide-generating structure and the peroxide-activating catalyst are located in each channel of the plurality of channels.

Clause 28. The replaceable air purification element of any of Clauses 22 to 27, wherein the air purification element comprises a surface having a texture to create turbulent airflow.

Clause 29. The replaceable air purification element of any of Clauses 22 to 28, wherein the air purification element comprises a curved airflow channel to create turbulent airflow.

Clause 30. The replaceable air purification element of any of Clauses 22 to 26, wherein the air purification element comprises a hollow fiber of a porous material.

Clause 31. The replaceable air purification element of any of Clauses 22 to 26 and 28, wherein the air purification element comprises a channel having a tapered end configured to create a vortex in airflow through the channel.

Clause 32. The replaceable air purification element of any of Clauses 22 to 26, wherein the peroxide-generating structure comprises one or more of a rod-shaped structure and a vane-shaped structure having a first electrode at least partially surrounded by a second electrode with an ionically conductive matrix disposed therebetween.

Clause 33. The replaceable air purification element of any of Clauses 22 to 32, wherein the peroxide-generating structure comprises a battery.

It will be understood that the configurations and/or approaches described herein are exemplary in nature, and that these specific embodiments or examples are not to be considered in a limiting sense, because numerous variations are possible. The specific routines or methods described herein may represent one or more of any number of strategies. As such, various acts illustrated and/or described can be performed in the sequence illustrated and/or described, in other sequences, in parallel, or omitted. Likewise, the order of the above-described processes can be changed.

The subject matter of the present disclosure includes all novel and non-obvious combinations and sub-combinations of the various processes, systems, and configurations, and other features, functions, acts, and/or properties disclosed herein, as well as any and all equivalents thereof.

The invention claimed is:

1. A system, comprising:
   an airflow passage configured to confine a flow of air and direct the flow of air toward a space; and
   an air purification element positioned in the airflow passage and configured to produce a peroxide to oxidize contaminants in air flowing through the airflow passage, the air purification element comprising a layered structure including:
   a peroxide-generating structure configured to produce the peroxide from a water vapor and oxygen in the air within the airflow passage, the peroxide-generating structure having a first electrode and a second electrode with an ionically conductive matrix disposed therebetween; and
   a matrix containing a peroxide-activating catalyst configured to activate peroxide produced, the matrix being arranged as an outermost layer of the air purification element to allow the contaminants to contact peroxide activated by the peroxide-activating catalyst, wherein
   the peroxide is produced upon application of a voltage across the first electrode and the second electrode, and
   the air purification element comprises a plurality of channels for airflow and the peroxide-generating structure and the matrix containing the peroxide-activating catalyst are located in each channel of the plurality of channels.

2. The system of claim 1, wherein the peroxide-generating structure comprises an electrocatalyst.

3. The system of claim 1, wherein the system comprises an aircraft, and the airflow passage in which the air purification element is positioned is configured to provide air to a cabin of the aircraft.

4. The system of claim 1, wherein the system comprises a personal respiration device.

5. The system of claim 1, wherein the system comprises a habitable fixed structure.

6. The system of claim 1, wherein the air purification element comprises an integrated unit configured to be removably placed in the airflow passage.

7. The system of claim 1, wherein the air purification element comprises a surface having a texture to create turbulent airflow.

8. The system of claim 1, wherein the air purification element comprises a curved airflow channel to create turbulent airflow.

9. The system of claim 1, wherein the air purification element comprises a channel configured to create a vortex in airflow through the channel.

10. An aircraft, comprising:
    a cabin;
    an airflow passage configured to confine a flow of air and direct the flow of air toward the cabin; and
    an air purification element positioned in the airflow passage and configured to produce a peroxide to oxidize contaminants in air flowing through the airflow passage, the air purification element including:
    a peroxide-generating structure configured to produce the peroxide from water vapor and oxygen in the airflow passage, the peroxide-generating structure including a first electrode separated from a second electrode by an ionically conductive matrix and being configured to produce the peroxide upon application of a voltage across the first electrode and the second electrode; and
    a matrix containing a peroxide-activating catalyst configured to activate the peroxide produced, the matrix containing the peroxide-activating catalyst being arranged as an outermost layer of the air purification element to allow the contaminants to contact peroxide activated by the peroxide-activating catalyst, wherein the air purification element comprises a plurality of channels for airflow, and wherein the peroxide-generating structure and the matrix containing the peroxide-activating catalyst are located in each channel of the plurality of channels.

11. The aircraft of claim 10, the air purification element comprises an integrated unit configured to be removably placed in the airflow passage.

12. The aircraft of claim 10, wherein the air purification element comprises a surface having a texture to create turbulent airflow.

13. The aircraft of claim 10, wherein the air purification element comprises a curved airflow channel to create turbulent airflow.

14. A system, comprising:
    an airflow passage configured to confine a flow of air and direct the flow of air toward a space; and
    an air purification element positioned in the airflow passage and configured to produce a peroxide to oxidize contaminants in air flowing through the airflow passage, the air purification element comprising a layered structure including:
    a photochemical peroxide-generating structure configured to produce the peroxide from a water vapor and oxygen in the air within the airflow passage when exposed to ultraviolet light; and a matrix containing a peroxide-activating catalyst configured to activate peroxide produced, the matrix being arranged as an outermost layer of the air purification element to allow the contaminants to contact peroxide activated by the peroxide-activating catalyst, wherein the air purification element comprises a plurality of channels for airflow and the peroxide-generating structure and the matrix containing the peroxide-activating catalyst are located in each channel of the plurality of channels.

15. The system of claim 14, wherein the photochemical peroxide-generating structure comprises titanium dioxide.

16. The system of claim 14, wherein the air purification element comprises a surface having a texture to create turbulent airflow.

17. The system of claim 14, wherein the system comprises an aircraft, and the airflow passage in which the air purification element is positioned is configured to provide air to a cabin of the aircraft.

18. The system of claim 14, wherein the system comprises a personal respiration device.

19. The system of claim 14, wherein the system comprises a habitable fixed structure.

20. The system of claim 14, wherein the air purification element comprises an integrated unit configured to be removably placed in the airflow passage.

\* \* \* \* \*